United States Patent [19]

Ponsford et al.

[11] Patent Number: 4,954,489
[45] Date of Patent: Sep. 4, 1990

[54] PENICILLINS HAVING A SUBSTITUTED ACRYLAMIDO SIDE CHAIN

[75] Inventors: Roger J. Ponsford; Andrew V. Stachulski, both of Betchworth, England

[73] Assignee: Beecham Group p.l.c, England

[21] Appl. No.: 333,554

[22] Filed: Apr. 5, 1989

[30] Foreign Application Priority Data

Apr. 6, 1988 [GB] United Kingdom ............... 8808032
Aug. 4, 1988 [GB] United Kingdom ............... 8818513
Sep. 26, 1988 [GB] United Kingdom ............... 8822511

[51] Int. Cl.$^5$ ............... A61K 31/43; C07D 499/12; C07D 499/54
[52] U.S. Cl. ............... 514/195; 514/196; 540/316; 540/328
[58] Field of Search ............... 540/316, 328; 514/195, 514/196

[56] References Cited

U.S. PATENT DOCUMENTS 4,235,774 11/1980 Preiss et al. ............... 540/328
4,416,880 11/1983 Boberg et al. ............... 540/328 X Primary Examiner—Werren B. Lone
Assistant Examiner—Vera C. Clarke
Attorney, Agent, or Firm—Jacobs & Jacobs

[57] ABSTRACT

Compounds of formula (I) and their salts and esters:

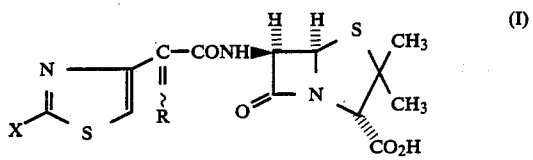

wherein X is hydrogen or a group $NHR^1$, wherein $R^1$ is hydrogen or an amino protecting group, and R is optionally substituted $C_{5-8}$ cycloalkyl or cycloalkenyl, are useful in the treatment of bacterial infections.

19 Claims, No Drawings

PENICILLINS HAVING A SUBSTITUTED ACRYLAMIDO SIDE CHAIN

This invention relates to novel β-lactam containing compounds, their preparation and their use, and in particular to a novel class of penicillins. These compounds have antibacterial properties, and therefore are of use in the treatment of bacterial infections in humans and animals caused by a wide range of organisms.

US-A-3,622,569, , US-A-4,416,880, US-A-4,782,162, US-A-4,500,716, GB-A-2,173,194 and JP-A-2,215,593 disclose β-lactam antibiotics containing a substituted acrylamido side chain.

We have now found a particular class of penicillin antibiotics containing a substituted acrylamido side chain that possesses high antibacterial activity and a high level of stability to bacterial β-lactamases.

The present invention accordingly provides a compound of formula (I) or a pharmaceutically acceptable salt or in-vivo hydrolysable ester thereof:

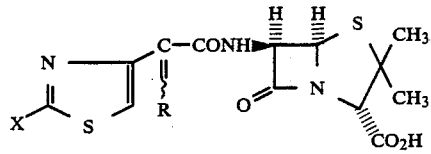

wherein X is hydrogen or a group $NHR^1$, wherein $R^1$ is hydrogen or an amino protecting group, and R is optionally substituted $C_{5-8}$ cycloalkyl or cycloalkenyl.

Substituents for a cycloalkyl or cycloalkenyl group include $C_{1-6}$ alkyl, such as methyl or t-butyl. The alkyl group may for example be attached at the 2-position of the ring.

Further suitable substituents for a cycloalkyl or cycloalkenyl group include hydroxy, $C_{1-6}$ alkoxy, aryl, halogen, trifluoromethyl and methylene optionally substituted by halogen.

When used herein the term 'aryl' includes phenyl and naphthyl optionally substituted with up to five, preferably up to three, groups selected from halogen, $C_{1-6}$ alkyl, phenyl, $C_{1-6}$ alkoxy, halo($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl, $C_{1-6}$ alkylcarbonyloxy, or $C_{1-6}$ alkylcarbonyl groups.

Preferably, X is the group $NHR^1$.

In particular, esters of compounds of formula (I) have been found to give a high level of oral absorption.

Compounds of the invention may exist in two or more tautomeric forms, e.g. those having the partial structures below:

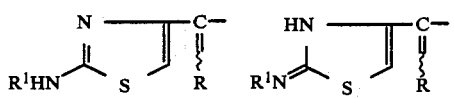

It should be understood that all tautomeric forms of the compound of formula (I) are included within the scope of the invention.

Suitable amino protecting groups $R^1$ are those well known in the art which may be removed under conventional conditions without disruption of the remainder of the molecule.

Examples of amino protecting groups $R^1$ include $C_{1-6}$ alkanoyl; benzoyl or benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl.

Particular values of R within the present invention include cyclohexyl, cyclooctyl, cyclohex-3-en-1-yl, 2-methylcyclohexyl, and 4-t-butylcyclohexyl.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

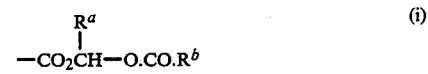

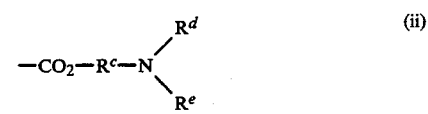

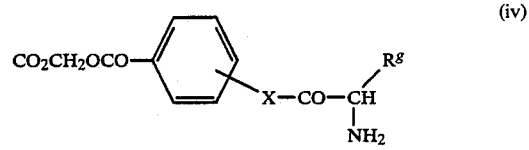

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and X is (preferably o) oxygen or (preferably o or p)NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)propyl, and (1-aminoethyl)carbonyloxymethyl; alkoxy-carbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

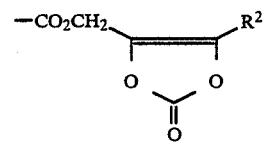

wherein $R^2$ is hydrogen, $C_{1-6}$ alkyl or phenyl.

Certain in-vivo hydrolysable esters of compounds of formula (I) have been found to be particularly well absorbed via the oral route, more particularly the acyl-oxyalkyl, such as the α-acetoxyethyl, esters.

Suitable pharmaceutically acceptable salts of the carboxy group of the compound of formula (I) include metal salts, eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylene-diamine, 1-ephenamine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins.

Some of the compounds of this invention may be crystallised or recrystallised from solvents such as methanol. In such cases solvates may be formed. This invention includes within its scope stoichiometric solvates including hydrates as well as compounds containing variable amounts of water that may be produced by processes such as lyophilisation.

Since the compounds of the formula (I) and their salts and in-vivo hydrolysable esters are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds of the formula (I) and their salts may be used for preparing the more pure forms used in the pharmaceutical compositions; these less pure preparations of the compounds of formula (I) and their salts should contain at least 1%, more suitably at least 5% and preferably from 10 to 49% of a compound of the formula (I) or salt thereof.

Compounds of the present invention may exist as either syn or anti isomers, or may exist as mixtures of syn and anti isomers containing at least 75% of one such isomer, or preferably at least 90% of one such isomer.

Herein the terms syn and anti refer to the configuration of the group R with respect to the carboxamido group, the syn-configuration (sometimes called the Z-configuration) being denoted thus:

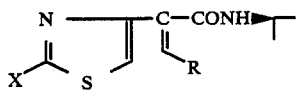

and the anti configuration (sometimes called the E-configuration) being denoted thus:

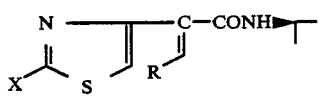

Preferred compounds of the present invention are the syn-isomers of the formula (IA):

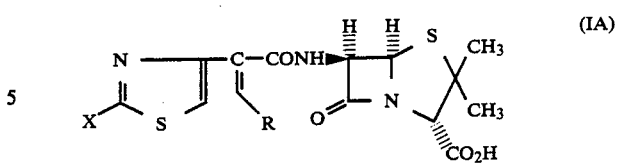

wherein R and X are as hereinbefore defined.

The compounds of formula (I) may be prepared by treating a compound of formula (II) or salt thereof:

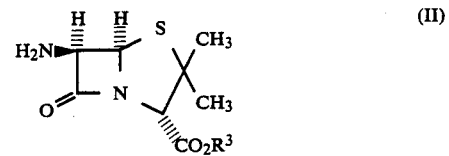

wherein the amino group is optionally substituted with a group which permits acylation to take place, and $R^3$ is hydrogen or a readily removable carboxyl blocking group; with an acylating agent derived from the acid of formula (III):

wherein Y is a group of formula:

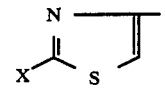

or a group which is convertable thereto, and R and X are as defined with respect to formula (I).

Any of the following reactions in any appropriate sequence may than be carried out:
(i) removal of any amino-protecting group $R^1$;
(ii) removal of any carboxyl blocking group $R^3$;
(iii) formation of a pharmaceutically acceptable salt;
(iv) conversion of a carboxyl group into an ester function such as an in vivo hydrolysable ester.
(v) conversion of group Y to a group of formula

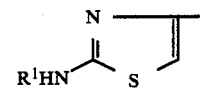

Suitable groups which permit aCylation to take place and which are optionally present on the amino group of the starting material of formula (II) include N-silyl, N-stannyl and N-phosphorus groups, for example trialkylsilyl groups such as trimethylsilyl, trialkyltin groups such as tri-n-butyltin, groups of formula —$PR^aR^b$ wherein $R^a$ is an alkyl, haloalkyl, aryl, aralkyl, alkoxy, haloalkoxy, aryloxy, aralkoxy or dialkylamino group, $R^b$ is the same as $R^a$ or is halogen or $R^a$ and $R^b$ together form a ring; suitable such phosphorus groups being —$P(OC_2H_5)_2$, —$P(C_2H_5)_2$,

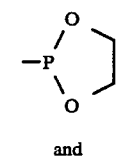

and

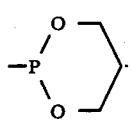

Suitable carboxyl-blocking derivatives for the group $CO_2R^3$ in formula (II) include salts and ester derivatives of the carboxylic acid. The derivative is preferably one which may readily be cleaved at a later stage of the reaction. Suitable salts include metal salts, such as those with sodium, potassium and lithium, a preferred salt is sodium.

Suitable ester-forming carboxyl-blocking groups are those which may be removed under conventional conditions. Such groups for $R^3$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl (benzhydryl), triphenylmethyl, adamantyl,2-benzyloxyphenyl, 4-methylthiophenyl, tetrahydrofuran-2-yl, tetrahydropyran-2-yl, pentachlorophenyl, p-toluenesulphonylethyl, methoxymethyl, a silyl, stannyl or phosphorus-containing group, such as described above, an oxime radical of formula $-N=CHR^4$ where $R^4$ is aryl or heterocyclic, or an in vivo hydrolysable ester radical such as defined above.

The carboxyl group may be regenerated from any of the above esters by usual methods appropriate to the particular $R^3$ group, for example, acid—and base—catalysed hydrolysis, or by enzymically—catalysed hydrolysis, or by hydrogenation under conditions wherein other parts of the molecule are unaffected.

A reactive N-acylating derivative of the acid of formula (III) is employed in the above process. The group $R^1$ in the acid of formula (III), when present, will be chosen such that the group $NHR^1$ does not react when the carboxy group in (III) is converted into the said N-acylating derivative. Thus, in many—although not all—of the suitable N-acylating derivatives of the acid (III) detailed below, $R^1$ cannot be hydrogen.

A preferred amino-protecting group $R^1$ in the intermediate of formula (III) is chloroacetyl, which $R^1$ group may suitably be removed from the product of formula (I) by treatment with sodium N-methyl dithiocarbamate.

Suitable N-acylating derivatives of the acid (III) include acid (III) halides, preferably the acid chloride or bromide. Acylation with an acid halide may be effected in the presence of an acid binding agent, for example a tertiary amine (such as triethylamine or dimethylaniline), an inorganic base (such as calcium carbonate or sodium bicarbonate), molecular sieves (such as type 4 Angstroms) or an oxirane, which binds hydrogen halide liberated in the acylation reaction. The oxirane is preferably a $(C_{1-6})$—1,2-alkylene oxide —such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, aqueous tetrahydrofuran, ethyl acetate, dimethylacetamide, dimethylformamide (DMF), acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (III) with a halogenating (eg chlorinating or brominating) agent such as phosphorus pentachloride, thionyl chloride or oxalyl chloride.

Alternatively, the N-acylating derivative of the acid (III) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as methanesulphonic acid and p-toluenesulphonic acid respectively). When a symmetrical anhydride is employed, the acylation reaction may be carried out in the presence of an organic base such as 2,6-lutidine as catalyst.

When a mixed anhydride is employed the N-acylating derivative is preferably prepared in the presence of an organic base such as triethylamine and/or N,N-diisopropylethylamine in a suitable solvent such as DMF at between $-50°$ C. and room temperature. Alternatively, the N-acylating derivative may be prepared from an alkali metal salt of the acid of formula (III), such as the sodium salt, in a suitable solvent such as DMF at between $-50°$ C. and room temperature. The N-acylating derivative of the acid of formula (III) so derived may then be reacted with a compound of formula (II). The acylation reaction may conveniently be carried out at $-50°$ C. to $+50°$ C. in a suitable solvent such as water, acetonitrile or DMF at a temperature of not more than $0°$ C. The reaction may be carried out in the presence of a suitable base such as triethylamine or sodium hydrogen carbonate.

A further method of forming the N-acylating derivative of the acid of formula (III) wherein X is hydrogen or a protected $NH_2$, is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at $-40°$ to $+30°$ C., if desired in the presence of an acid binding agent such as triethylamine. A catalyst such as 4-dimethylaminopyridine may optionally also be added.

Other suitable acylating agents derived from the acid of formula (III) are thioesters of formula (IV)

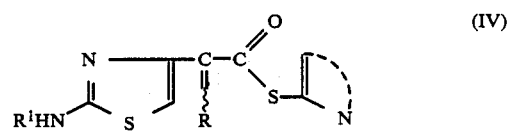

wherein R and $R^1$ are as hereinbefore defined and

represents a 5- or 6-membered heterocyclic ring, which may contain, in addition to the nitrogen atom, one or two further heteroatoms, selected from oxygen, nitrogen and sulphur and which may be substituted or fused to a benzene ring which may itself be substituted.

Particular acylating agents derived from the acid of formula (III) are the thio esters (IVa) or (IVb)

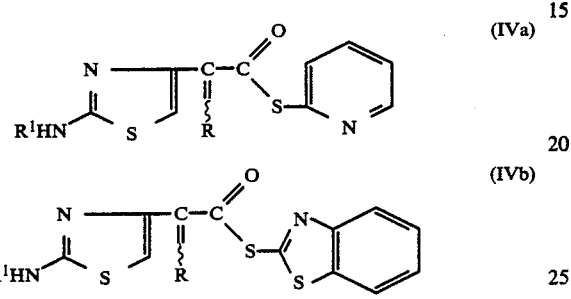

wherein R and R¹ are as hereinbefore defined.

Compounds of the formula (IVa) and (IVb) may be prepared by treatment of the acid (III) with 2,2'-dipyridyldisulphide or 2,2'-dibenzothiazolyldisulphide respectively, in the presence of triphenylphosphine, analogously to the routes described in EP-A-0037380. Conveniently, in compounds of the formula (IVa) and (IVb), R¹ may be hydrogen.

Other suitable N-acylating derivatives of acid (III) include the acid azide; the activated esters derived from cyanomethanol; p-nitrophenol; 2,4-dinitrophenol; thiophenol; halophenols, including pentachlorophenol; monomethoxyphenol; N-hydroxy succinimide; N-hydroxybenzotriazole or 8-hydroxyquinoline; or include amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxolinium-3-sulphonate or N-7-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$ —$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

Compounds of formula (III) may be prepared by routes analogous to those disclosed in US-A-3,622,569, US-A-4,416,880, US-A-4.500,716 and Ep-A-0 161 617.

In particular compounds of formula (III) may be prepared by condensation of an aldehyde of formula RCHO with an ester, such as the methyl ester, of the acid $YCH_2COOH$, wherein R and Y are as hereinbefore defined.

The acid of formula $YCH_2COOH$ wherein Y is optionally protected 2-amino-thiazol-4-yl, and its esters, are believed to be novel compounds and form a further aspect of the invention. Their preparation is described hereinbelow in the Examples.

Any of the following reactions in any appropriate sequence may then be carried out:

(i) conversion of Y to a group of formula:

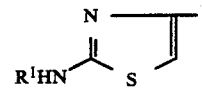

(ii) separation of E and Z isomers,
(iii) deamination of a group of formula:

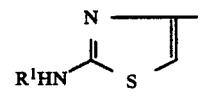

(iv) removal of a protecting group R¹ when present, and
(v) hydrolysis of an ester of the acid of formula (III).

The condensation reaction is typically carried out at low temperatures, e.g. about $-20°$ C., in the presence of a base such as piperidine, or by reflux with acetic acid-piperidine, catalysis in benzene or toluene and azeotropic removal of water.

Separation of E and Z isomers can be effected by chromatography, for example by silica gel chromatography using an ethyl acetate-hexane solvent system.

Processes for the deamination of an aminothiazole group to give a thiazole group are known and are described in J. Chem. Soc, 1973, 541, (J. Cadogan and G. Molina).

Advantageously, the removal of R¹, when R¹ is a protecting group such as N-acyl, and the hydrolysis of the ester group can be carried out in a single step, for example by refluxing with excess base, such as sodium hydroxide, in an aqueous solvent system such as aqueous dioxan.

Y may be any suitable group, but it is preferred that Y be an α-halo acetyl group (or an acetyl group which can be α-halogenated), the conversion of which may be effected by condensation with optionally N-acylated thiourea. The condensation reaction is typically carried out at elevated temperatures in an inert solvent such as dimethyl formamide.

Aldehydes of formula RCHO are commercially available or can be obtained by oxidizing commercially available alcohols, using a suitable oxidizing agent such as pyridinium chlorochromate or dichromate.

Aldehydes of formula RCHO can also be obtained by deetherifying a corresponding enol ether of formula $R=CHOR^{11}$ wherein $R^{11}$ is alkyl such as methyl.

Compounds of formula $R=CHOR^{11}$ may be prepared by an analogous procedure to that outlined in EP-A-0 159 784.

Certain of the compounds of formula. (III) are novel, and these novel compounds and their derivatives also form a part of the present invention.

The present invention also provides a pharmaceutical composition which comprises a compound of formula (I) or a pharmaceutically acceptable salt or in vivo hydrolysable ester thereof and a pharmaceutically acceptable carrier. The compositions of the invention include those in a form adapted for oral, topical or parenteral use and may be used for the treatment of the infection in mammals including humans.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, dependinq on the method of administration. Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) is administered in the above-mentioned dosage range.

Compounds of the present invention are characterised by increased stability to $\beta$-lactamase producing organisms when compared to synthetic penicillins in commercial use such as amoxycillin.

The compound of the invention of formula (I) may therefore be used as the sole therapeutic agent in compositions of the invention or may be used in combination with other antibiotics or with a $\beta$-lactamase inhibitor.

Advantageously the compositions also comprise a compound of formula (V) or a pharmaceutically acceptable salt or ester thereof:

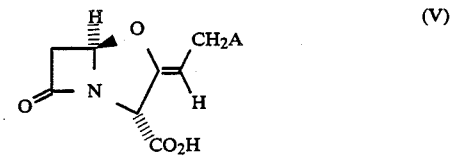

(V)

wherein A is hydroxyl; substituted hydroxyl; thiol; a qroup of formula $SO_2R^5$ wherein $R^5$ is $C_{1-6}$ alkyl: substituted thiol; amino; mono- or di-hydrocarbyl substituted amino; mono- or di-acylamino; an optionally substituted triazolyl group; or an optionally substituted tetrazolyl group as described in EP 0 053 893.

A further advantageous composition comprises an antibiotic compound according to the invention and a pharmaceutically acceptable carrier or excipient together with a $\beta$-lactamase inhibitor of formula (VI) or a pharmaceutically acceptable salt or in vivo hydrolysable ester thereof:

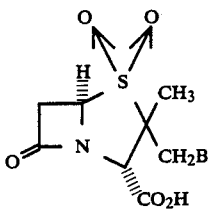

(VI)

wherein B is hydrogen, halogen or a group of formula:

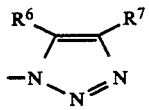

in which $R_6$ and $R_7$ are the same or different and each is hydrogen, $C_{1-6}$ alkoxycarbonyl, or carboxy or a pharmaceutically acceptable salt thereof.

Further suitable β-lactamase inhibitors include 6-alkylidene penem of formula (VII) below:

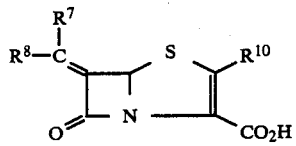

(VII)

or a pharmaceutically acceptable salt or in vivo hydrolysable ester thereof, wherein $R^8$ and $R^9$ are the same or different and each represents hydrogen, or a $C_{1-10}$ hydrocarbon or heterocyclic group optionally substituted with a functional group; and $R^{10}$ represents hydrogen or a group of formula $R^a$ or $-SR^a$ where $R^a$ is an optionally substituted $C_{1-10}$ hydrocarbon or heterocyclic group, as described in EP-A-0 041 768.

Other suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

Antibiotic compounds of the present invention are active against a broad range of bacteria, in particular they are useful for treatment of respiratory tract and urinary tract infections in humans and mastitis in cattle. It should be stressed that a particular advantage of certain compounds of the invention is their stability to β-lactamase enzymes and they are therefore effective against β-lactamase-producing organisms.

The antibiotic compounds of the present invention are active against both Gram-negative and Gram-positive organisms including *E.coli*, in particular ESS and NCTC 10418; *H.influenzae*, in particular Q1 and NEMC 1; *S.aureus* such as Oxford, Russell and MB 9; *S.pyogenes* such as CN10; *S.agalactiae* such as 2798; *S.pneumoniae* such as PU7 and 1761; and *B.catarrhalis* such as Ravasio.

The following Examples illustrate the preparation of the compounds of the present invention.

EXAMPLE 1

Sodium 6β-[Z-2-(2-aminothiazol-4-yl)-3-cyclohexyl]-propenamidopenicillanate (a) Methyl (E, Z) [2-(2-chloro-1-oxoethyl)-3-cyclo-hexyl]propenoate Methyl-4-chloroacetoacetate (7.53g), cyclohexanecarboxaldehyde (5.33g), piperidine (0.13ml) and glacial acetic acid (0.36ml), were stirred in benzene (10ml) under reflux, with a water separator, for 2h. After this time the reaction appeared complete by t.l.c. The reaction mixture was allowed to cool and taken up in ether. This solution was washed three times with water, once with brine, dried, filtered and evaporated to yield a mobile yellow oil. This was flash chromatographed on $SiO_2$ eluting with ethyl-acetate-hexane mixtures to give 2.50g of the desired product (mixed isomers); δ(CDCCl$_3$, 90MHz) 0.8–2.0 (10H, 2m), 2.0–2.86 (1H, m), 3.75+3.81 (3H, 2s) 4.32+4.35 (2H, 2s), 6.84+6.91 (1H, 2d, J=11Hz). Isomer ratio 4:3.

(b) Methyl (E, Z) 2-(2-acetamidothiazol-4-yl)-3-cyclo-hexyl]propenoate

Methyl (E, Z) [2-(2-chloro-1-oxoethyl)-3-cyclohexyl]propenoate (3.70g) and N-acetylthiourea (1.785g) were stirred in dry dimethylformamide (DMF) (10ml) at 80°–90° C. for 2h, when the reaction appeared complete by t.l.c. The mixture was cooled, partitioned between ethyl acetate and water and the organic phase washed four times with water, once with brine, dried, filtered and evaporated to yield a gum. This was chromatographed on $SiO_2$ eluting with ethyl acetate-hexane mixtures, to give, firstly, the crystalline Z-isomer (1.92g), mp 146°–149° C. (from ether-hexane); ν$_{max}$ (CHCl$_3$) 3425 1710 (br), 1560 (sh), 1535, 1510 (sh) cm$^{-1}$; δ(CDCl$_3$, 250MHz) 1.24–1.73 (10H, 2M), 2.18 (3H, s), 2.55 (1H, m), 3.86 (3H, s), 6.55 (1H, d, J=10Hz), 6.93 (1H, s), 9.88 (1H, br, s): (Found: C 58.5; H, 6.5; N, 9.3; S, 10.3. $C_{15}H_{20}N_2O_3S$ requires C, 58.4; H, 6.5; N, 9.1; S, 10.4%). Further elution of the column gave the E-isomer (0.85g), which was distinguished principally by δ6.93 (1H, d, J=10Hz).

(c) Methyl 2-acetamidothiazol-4-acetate

Methyl-4-chloroacetoacetate (11.54ml), N-acetylthiourea (11.8g) and 4A molecular sieves (10g) were stirred in dry, distilled dimethylformamide (DMF) (50ml) at 50° C., for 23h. After this time the reaction appeared complete by t.l.c. The mixture was cooled and filtered through a dicalite pad. The residue was washed with DMF and tetrahydrofuran and the resultant filtrates diluted with water. This solution was washed five times with ethyl acetate; the organic washes were combined, dried, filtered and evaporated to give a yellow oil. This was triturated under water whereupon a white precipitate formed. This was cooled to complete and the resultant solid filtered off, washed with cold water and dried to give the desired product (14.63g) as a white crystalline solid, m.p. 122°–123° C. (from ethyl acetate-hexane); ν$_{max}$ (nujol) 3175 (w), 1740, 1655, 1560 and 1543cm$^{-1}$; δ[(CD$_3$)$_2$SO, 60MHz]2.1 (3H, s). 3.6 (3H. s). 3.7 (2H. s). and 6.9 (1H. s). (Found: C, 44.9; H, 4.7; N, 13.4; S, 15.3. $C_8H_{10}N_2O_3S$ requires: C, 44.9; H, 4.7; N, 13.1; S, 15.0%). The mother liquors were concentrated to low volume and cooled to yield a second crop of the desired material (2.54g) which was slightly less pure by NMR.

(d) Methyl (E,Z) 2-(2-acetamidothiazol.4-yl)-3-cyclo-hexyl]propenoate

Methyl 2-acetamidothiazol-4-acetate (1.07g), cyclohexanecarboxaldehyde (0.61ml), glacial acetic acid (0.29ml) and piperidine (0.49ml) were stirred in benzene (10ml) under reflux, with a water separator, for 3 days. By t.l.c. the reaction was then near completion; the reaction mixture was allowed to cool and evaporated to low volume. The residue was taken up in ethyl acetate and washed three times with water, once with brine, dried, filtered and evaporated to a foam. This was flash chromatographed on silica gel, eluting with ethyl acetate-hexane mixtures, to give firstly the Z isomer as an oil (0.580g). This was triturated under hexane and a little ether added. The resultant solid was filtered off to give the solid Z-isomer (0.525g) [spectral data recorded in Example 1b]. Further elution of the column produced the noncrystalline E-isomer (0.597g) [spectral data recorded (same reference)].

(e) Z-[2-(2-aminothiazol-4-yl)-3-cyclohexy]propenoicacid

Methyl Z-[2-(2-acetamidothiazol-4-yl)-3-cyclohexyl]-propenoate. (1.92g) was dissolved in dioxan (20ml). 1M NaOH (31ml) was added and the mixture stirred at 95° C. for 3h, when reaction appeared complete by t.l.c. The mixture was cooled and evaporated to dryness. The residue was taken up in water and washed twice with ether (each organic phase was backwashed with a little water). The combined aqueous phase was acidified with 5M HCl to pH4, whereupon a fine, pale precipitate formed. This was cooled to complete and the precipitate filtered off, washed with ice-cold water and dried to give the desired product (1.34g); $\nu$max (KBr) 3600–2200 (br), 1690 (sh), 1629, 1560, 1528cm$^{-1}$; $\delta$[(CD$_3$)$_2$CO, 250MHz]1.26–1.71 (10H, 2m), 2.63 (1H, m), 6.46 (1H, d, J=10Hz), 6.52 (1H, s). [Found: M 252.0929. C$_{12}$H$_{16}$N$_2$O$_2$S requires M 252.0932).

(f) Sodium 6$\beta$-[Z-2-(2-aminothiazol-4-yl)-3-cyclohexyl]-propenamidopenicillante Z-[2-(2-Aminothiazol-4-yl)-3-cyclohexyl]propenoic acid (0.50g) and 1-hydroxybenzotriazole monohydrate (0.32g) were stirred in dry DMF (6ml) at 0° C. whilst N,N'-dicyclohexylcarbodi-imide (0.43g) was added. The mixture was allowed to warm to room temperature and stirred under argon for 2.75h. T.l.c. showed active ester to have formed. The mixture was filtered into a stirring solution of 6-aminopenicillanic acid (0.50g) and 1N NaOH (2.30ml) in H$_2$O (6ml) (filtered solid was washed with fresh DMF). The mixture was stirred at room temperature for 2.5h, when t.l.c. showed reaction to be complete. The mixture was filtered, the solid washed with water and THF and the filtrate evaporated to dryness, taken up in water and adjusted to pH8 with NaHCO$_3$ (aq). The aqueous phase was washed twice with ethyl acetate: ether (1:1) (backwashing each time with water). The combined aqueous was acidified to pH2 with 1M HCl and extracted into ethyl acetate. This organic phase was washed twice with water and then stirred over water whilst NaHCO$_3$ (aq) was added to pH 6.5. The phases were separated and the organic washed once with water. The combined aqueous was evaporated to low volume and freeze dried to give impure product (330mg). This was chromatographed on HP20SS to give the title penicillin (75mg); $\nu$max (KBr) 1765, 1655 (sh), 1609, 1526cm$^{-1}$; $\delta$(D$_2$) 1.21–1.66 (10H, 2m), 1.51 and 1.61 (6H, 2s), 2.24 (1H, m), 4.23 (1H, s), 5.60 (2H, dd), 6.15 (1H, d, J=10Hz), 6.44 (1H, s); m/e 473 (MH$^+$), 495 (MNa$^+$).

EXAMPLE 2

Sodium 6$\beta$-[Z-(2-aminothiazol-4-yl)-3-cyclooctyl]propenamidopenicillanate

(a) Methyl (E, Z) [2-(2-chloro-1-oxoethyl)-3-cyclo-octyl]propenoate

Methyl 3-oxo-4-chlorobutanoate (3.0g) and cyclooctane-carboxaldehyde (2.82g) were stirred with piperidine (0.05ml) under argon at −20° C. For ease of stirring the mixture was allowed to warm slowly to −10° C.–0° C. After 4h the reaction mixture was diluted with ethyl acetate and washed with ice-cold 1M hydrochloric acid (3×), water and brine. Evaporation of the dried extract gave a near-colourless oil (5.7g) which was subjected to chromatography on silica gel eluting with 2% ethyl acetate in hexane, affording the product isomers (0.84g). It was possible to separate the individual isomers but experimentally they were more easily separated at the next stage. The first-eluted isomer showed $\nu$max (CHCl$_3$) 1710 (br, s), 1630, 1465, 1435cm$^{-1}$; $\delta$(CDCl$_3$, 250MHz) 1.40–1.80 (14H, m), 2.59 (1H. m), 3.80 (3H, s), 4.37 (2H, s), and 7.04 (1H, d, J 11Hz). The second eluted isomer was distinguished principally by $\delta$6.97 (1H, d, J 11Hz). Found: M, 272.1183. C$_{14}$H$_{21}$O$_3$Cl requires M, 272.1180.

(b) Methyl (E,Z)-[2-(2-acetamidothiazol-4-yl)-3-cyclo-octyl]-propenoate

Methyl (E, Z) [2-(2-chloro-1-oxoethyl)-3-cyclooctyl]-propenoate (1.12g) was dissolved in anhydrous dimethylformamide (2ml) and heated with N-acetylthiourea (0.49g) at 90° C. After 1.25h t.l.c. analysis indicated complete consumption of the starting material. The reaction mixture was cooled, poured onto ice-water and extracted with ethyl acetate. The organic phase was separated, washed with water (3x) and brine, dried and evaporated to a yellow oil (1.25g). Chromatography on silica gel, eluting with ethyl acetate-hexane mixtures, afforded firstly the crystalline Z-isomer (0.44g), m.p. 142°–143° C. (from ethyl acetate-hexane), $\delta_{max}$ (KBr) 3413(w), 1719, 1655, 1560cm$^{-1}$; $\delta$(CDCl$_3$, 250MHz) 1.40–1.80 (14H, m), 2.20, (3H, s), 2.83 (1H, m), 3.86 (3H, s), 6.64 (1H, d, J 1Hz), 6.92 (1H, s), and 9.63 (1H, br, s). (Found: C, 61.0; H, 6.8; N, 8.3; S, 9.4. C$_{17}$H$_{24}$N$_2$O$_3$S requires C, 60.7; H, 7.1; N, 8.3; S, 9.5%). Further elution gave the non-crystalline E-isomer (0.21g) which was distinguished principally by $\delta$7.05 (1H, d, J 11Hz).

(c) Z-[2-(2-aminothiazol-4-yl)-3-cyclooctyl]propenoic acid

Methyl Z-[2-(-acetamidothiazol-4-yl)-3-cyclooctyl]-propenoate (252mg) in purified dioxan (2.5ml) was heated with 1M sodium hydroxide (2ml) at 90°–95° C. After 5h t.l.c. analysis indicated essentially complete conversion to a single more polar material. The solution was evaporated to dryness, dissolved in water and washed twice with ether, backwashing each time with a little water. The combined aqueous extracts were acidified to pH3 using 5M hydrochloric acid then cooled to complete precipitation. The solid was filtered, washed with water and dried to give light brown material (200mg) which was purified by dissolving in dilute aqueous sodium hydroxide followed by reprecipitation with aqueous hydrochloric acid. Filtration, washing with water and drying afforded the pure acid (158mg); $\nu$max (KBr) 1695, 1628, 1565 and 1530cm$^{-1}$; $\delta$(CD$_3$)$_2$SO, 250MHz)1.25–1.75 (14H, m), 2.67 (1H, m), 6.37 (1H, d, J 10Hz), 6.37 (1H, s), and 7.04 (2H, br, s). (Found: M, 280.1246. C$_{14}$H$_{20}$N$_2$O$_2$S requires M, 280.1246).

(d) Sodium 6$\beta$-[Z-2-(2-aminothiazol-4-yl)-3-cyclooctyl]-propenamidopenicillanate Z-[2-(2-Aminothiazol-4-yl)-3-cyclooctyl]propenoic acid (280mg) and 1-hydroxybenzotriazole monohydrate (160mg) were dissolved in anhydrous dimethylformamide (2ml) and stirred at 0° C. N, N'-Dicyclohexylcarbodi-imide (215mg) was added and the mixture allowed to regain ambient temperature. After 2h the precipitate was filtered off and the filtrate added dropwise to a solution of 6-aminopenicillanic acid (260mg) in water (1ml) containing 1M sodium hydroxide (1.2ml). Stirring was continued at ambient temperature; after 2.5h t.l.c. analysis indicated complete consumption of starting material. The reaction mixture was filtered, the filtrate was evaporated to near dryness and the residue partitioned between water and ether: ethyl acetate, 1:1. The aqueous phase was separated, the organic extract was backwashed with water and the whole sequence repeated once. The combined aqueous extracts were acidified to pH3.8 when a facile deposition of solid occurred. The mixture was cooled and filtered; the precipitate was washed with water and dried to an off-white solid (392mg). Chromatography on silica gel was effected using ethyl acetate: propan-2-ol: water, 10:3:1 as eluant. Product-rich fractions were assessed by t.l.c., concentrated to low volume, adjusted to pH6.5–7.0 using sodium hydrogen carbonate solution, again concentrated and lyophilised to give the penicillin sodium salt (334mg). The earlier column fractions contained pure Z-isomer; later fractions contained 5–10% E-isomer as assessed by n.m.r. The Z-isomer showed $\nu$max (K8r) 1765, 1650 (sh), 1611, 1521cm$^{-1}$; $\delta$(CD$_3$)$_2$CO+D$_2$O, 1:1, 250MHz]1.40–1.80 (14H, m), 1.55, 1.63 (6H, 2s), 2.53 (1H, m), 4.22 (1H, s), 5.65 (2H, dd), 6.25 (1H, d, J 11Hz), and 6.42 (1H, s); m/e 501 (MH+), 479 (MH—Na+H+).

EXAMPLE 3

Sodium 6$\beta$-Z-2-(thiazol-4-yl)-3-cyclohexyl]-propenamidopenicillanate (a) Z-2-(thiazol-4-yl)-3-cyclohexy]propenoic acid Z-[2-(2-Aminothiazol-4-yl)-3-cyclohexyl]propenoic acid (Example 1; 126mg) was dissolved in tetrahydrofuran (3ml) and added dropwise to a stirred solution of amyl nitrite (117mg) in the same solvent (3ml) at 60° C. (Cf. J.Cadogan and G.Molina, *J.Chem.Soc.*, 1973, 541). After stirring at the same temperature for 1h, the solution was evaporated to near dryness, dissolved in ethyl acetate (10ml) and washed once with water. Acidic material was extracted with dilute sodium hydrogen carbonate solution (5×10ml), then the basic extracts were acidified to pH2 using HCl and re-extracted with ethyl acetate (20ml). The organic extract was washed with water, brine, dried and evaporated to a red oil (59mg). Chromatography on silica gel, eluting with methanol-chloroform mixtures, afforded the title acid as a pale red gum (22mg); $\delta$ (CDCl$_3$, 90MHz) 0.9–1.9 (10H, m), 3.2 (1H, m), 6.74 (1H, d, J 10Hz), 7.43 (1H, d, J 2Hz) and 8.77 (1H, d, J 2Hz).

(b) Sodium 6$\beta$-Z-[2-(thiazol-4-yl)-3-cyclohexyl]-propenamidopenicillanate Z-[2-(Thiazol-4-yl)-3-cyclohexyl]propenoic acid (80mg) and 1-hydroxybenzotriazole (54mg) were dissolved in dimethylformamide (2ml). The solution was stirred at 0° C. while N, N'-dicyclohexylcarbodi-imide (73mg) was added, then allowed to regain ambient temperature and stirred for 2h. The precipitated solid was filtered and the filtrate added to a solution of 6-aminopenicillanic acid (86mg) in water (1ml) containing 1M NaOH (0.4ml). This mixture was stirred at ambient temperature for 2h, after which t.l.c. analysis indicated complete reaction. The mixture was filtered, the filtrate was evaporated to dryness and the residue partitioned between water containing a little sodium hydrogen carbonate solution and ether: ethyl acetate, 1:1 (2×10ml). Each organic wash was backwashed with a little water, and the total aqueous phase was acidified to pH2 and extracted with ethyl acetate (2×20ml). The organic extract was washed with water (4×), then water was added and the pH adjusted to 7 with stirring using sodium hydrogen carbonate solution. The aqueous phase was separated, the organic phase was washed with a further portion of water and the total aqueous phase lyophilised to give crude product (161mg). Chromatography on silica gel, eluting with ethyl acetate: isopropanol: water mixtures afforded the title penicillin (112mg); $\nu$max (KBr) 1769, 1662, 1611, 1506cm$^{-1}$; $\delta$(D$_2$O, 250MHz) 1.10–1.40 and 1.50–1.80 (10H, 2m), 1.51, 1.61 (6H, 2s), 2.34 (1H, m), 4.22 (1H, s), 5.63 (2H, dd), 6.40 (1H, d, J 10Hz), 7.42 (1H, d, J 2Hz) and 8.92 (1H, d, J 2Hz); m/e 436 (MH—Na+H+), 458 (MH+).

EXAMPLE 4

1-Acetoxyethyl 6$\beta$-Z-[2-(2-aminothiazol-4-yl)-3-cyclohexyl]-propenamidopenicillanate 6$\beta$-Z-[2-(2-Aminothiazol-4-yl)-3-cyclohexyl]-propenamidopenicillanic acid (0.15g) in anhydrous dimethylformamide (1ml) was treated with triethylamine (0.093ml) then stirred at 0° C. while 1-bromethyl acetate (0.084g) was added. The mixture was allowed to regain ambient temperature and stirred for 2h, after which time t.l.c. analysis showed very little starting material. The mixture was diluted with ethyl acetate (5ml) and washed sequentially with 5% aqueous citric acid, brine, saturated aqueous sodium hydrogen carbonate and again with brine (3×). The final organic phase was dried and evaporated to a pale yellow oil, which was subjected to chromatography on silica gel, eluting with ethyl acetate: hexane, 1:1. Appropriate fractions were pooled and evaporated to a clear oil which solidified on trituration with ether to give the title ester (77mg); $\nu$max (KBr) 1765, 1656, 1612, 1523cm$^{-1}$; $\delta$(CD$_3$)$_2$CO], inter al., 1.54, 1.65 (6H, 2s), 4.41, 4.44 (1H, 2s), 5.68. 5.80 (2H, 2dd), 6.22 (1H, d. J=10Hz), 6.36 (1H, brs), 6.40 (2H, brs, D$_2$O exchanged), 6.91 (1H. m). 8.10 (1H, d. J=7.5Hz, D$_2$O exchanged); m/e 537 (MH+).

EXAMPLE 5

Sodium 6β-[[Z-2-(2-aminothiazol-4-yl)-3-(2-methyl)cyclohexy]-propenamido]penicillanate

(a) (E,Z)-1-(Methoxymethylene)-2-methylcyclohexane (Methoxymethyl)triphenyl phosphonium chloride (3.43g) was suspended in anhydrous tetrahydrofuran (10ml) and stirred under argon at 0° C. 1M Lithium hexamethyldisilazide in the same solvent (10ml) was added via a syringe and the mixture was allowed to regain ambient temperature while stirring for 0.5h, then cooled to −10° C. while 2-methylcyclohexanone (1.20ml 1.12g) was added. After stirring at 20° C. for 16h, the reaction mixture was diluted with water and extracted with ether (2×). The combined organic extracts were washed with water and brine, dried and evaporated to give crude product which was flash-chromatographed on silica gel, eluting with n-hexane. Product-rich fractions were assayed by t.l.c., pooled, evaporated and subjected to Kugelrohr distillation to afford the enol ether (0.76g) as a virtually 1:1 mixture of E and Z isomers; $\nu$max (CHCl$_3$) 1680, 1460, and 1450(sh)cm$^{-1}$; δ(CDCl$_3$, 60MHz) 1.05 (3H, 2d), 1.20–2.10 (9H, m), 3.50 (3H, 2s), and 5.70 (1H, br s).

(b) Methyl (E,Z)-[2-(2-acetamidothiazol-4-yl)-3-(2-methyl)cyclohexyl]-propenoate (E,Z)-1-(Methoxymethylene)-2-methylcyclohexane (0.76g) in a mixture of tetrahydrofuran (5ml), water (5ml) and methanol (2ml) was stirred with toluene 4-sulphonic acid hydrate (1.0g) at ambient temperature. When no enol ether could be seen by t.l.c., the solution was concentrated to low volume, neutralised with saturated aqueous NaHCO$_3$ and extracted with ether (2×). The combined organic extracts were washed with water and brine, dried and evaporated to a nearcolourless oil (0.50g) which exhibited δ(CDCl$_3$, 60MHz), inter alia, 9.8 (0.5H, d) and 10.0(0.5H, s). This material was condensed with methyl 2-acetamidothiazol 4-acetate (0.85g) according to the procedure of Example 1 (d). Flash chromatography of the crude product (0.95g) on silica gel, eluting with ethyl acetatehexane mixtures, afforded firstly the title Z-ester (85mg) as a1:1 mixture of isomers; δ(CDCl$_3$, 250MHz), inter alia, 2.22, 2.23 (3H, 2s), 3.85 (3H, s) 6.49 (1H, d, J=10Hz), and 6.80–7.00 (1H,m). Further elution gave the E-ester (77mg); δ(CDCl$_3$, 250MHz), inter alia, 2.21, 2.22 (3H,2s), 3.73 (3H,2s), 6.81, 6.82 (1H,2s), and 6.92 (1H,d,J=11Hz).

(c) Z-[2-(2-Aminothiazol-4-yl)-3-(2-methyl)cyclohexyl]-propenoic acid

Methyl Z-[2-(2-aminothiazol-4-yl)-3-(2-methyl)cyclohexyl]propenoate (80mg) was hydrolysed with 1M sodium hydroxide (5 equivalents) as described in Example 1 (e). After acidification with 5M HCl to pH2, the product was extracted with ethyl acetate (2×) and the combined organic extracts were washed with water (2×) and brine, then dried and evaporated to dryness. Flash chromatography of the residue on silica gel, eluting with ethyl acetate: isopropanol: water mixtures, followed by pooling and evaporation of appropriate fractions, afforded the title acid (39mg, isomers); δ[CD$_3$)SO, 250MHz]0.79 (3H, 2d, J=7Hz), 1.00–1.80 (9H,m), 2.08, 2.68 (1H, 2m), 6.19, 6.51 (1H, 2d, J=10.5Hz), 6.35, 6.37 (1H, 2s), 7.01 and 7.05 (2H, 2br s). (Found: M, 266.1092. C$_{13}$H$_{18}$N$_2$O$_2$S requires M, 266.1089).

(d) Sodium 6β-[[Z-2-(2-aminothiazol-4-yl)-3-(2methyl)cyclohexyl]-propenamido]penicillanate Z-[2-(2-Aminothiazol-4-yl)-3-(2-methyl)cyclohexyl]-propenoic acid (35mg) was coupled to 6-amino-penicillanic acid (34mg) using the active ester procedure as described in Example 1 (f). The crude product (39mg) was purified by flash chromatography on silica gel, eluting with ethyl acetate:isopropanol:water, 15:3:1, then 10:3:1 and finally 5:3:1. Product rich fractions were assessed by t.l.c., combined, concentrated to low volume, adjusted to pH 6.5 using aqueous NaHCO3 and freeze-dried to give the title penicillin (41mg) as a mixture of isomers; $\nu$max (KBr) 1767, 1660 (sh), 1610, 1526, and 1510cm$^{-1}$; δ[(CD$_3$)$_2$ CO+D$_2$O, 1:1], inter alia, 0.85–0.95 (3H, m), 1.00–2.00 (9H, m), 1.59, 1.64, 1.65 (6H, 3s), 2.68 (1H, m), 4.23, 4.24 (1H, 2s), 5.71 (2H, m), 6.15, 6.18, 6.55 (1H, 3d, J=10–11Hz), and 6.42 (1H, s); m/e 465 (MH—Na+H$^+$) and 487 (MH$^+$).

EXAMPLE 6

Sodium 6β[[Z-2-(2-aminothiazol-4-yl)-3-(4-trans-t-butyl)cyclohexyl]propenamido]penicillanate

(a) (R,S)-1-(Methoxymethylene)-4-t-butylcyclohexane (Methoxymethyl)triphenylphosphonium chloride (5.14g) was reacted with 4-t-butyl cyclohexanone (2.31g) in tetrahyrofuran (4ml) as described in Example 5(a) After chromatography the crude product (2.4g) was subjected to Kugelrohr distillation to afford the enol ether (1.33g); $\nu$max (CHCl$_3$) 1690 and 1365cm$^{-1}$; δ(CDCl$_3$), inter alia, 0.85 (9H, s), 3.55 (3H, s), and 5.85 (1H, br s). (Found: C, 79.25; H, 12.2. C$_{12}$H$_{22}$O requires C, 79.1; H, 12.1%).

(b) Cis-and trans-(4-t-butyl)cyclohexanecarboxaldehyde (R,S)-1-(Methoxymethylene)-4-t-butylcyclohexane (1.25g) was stirred with toluene 4-sulphonic acid hydrate (1.52g) in tetrahydrofuran: water (1:1, 10ml) at ambient temperature. After 29h, when no starting material was visible by t.l.c, saturated aqueous NaHCO$_3$ (20ml) was added and the mixture was extracted with ether (2x). The combined organic extracts were washed with water and brine, dried and evaporated to give the title aldehyde (1.11g) as a mixture of cis- and transisomers; $\nu$max (CHCl$_3$) 2720 (m), 1720, 1450, and 1365cm$^{-1}$; δ(CDCl$_3$, 60MHz), inter alia, 0.85, 0.90 (9H,2s) and 9.8 (1H,m). (The aldehyde was described by B. Cross and G.H. Whitham, J.Chem.Soc., 1960, 3892).

(c) Methyl (E,Z)-[2-(2-acetamidothiazol-4-yl)-3-(trans-4-t-butyl)-cyclohexyl]propenoate A mixture of cis-and trans-(4-t-butyl)cyclohexanecarboxaldehyde (1.11g) was condensed with methyl 2-acetamidothiazol-4-acetate (1.41g) as described in Example 1 (d). The crude product (2.36g) was flash-chromatographed on silica gel, eluting with ethyl acetate-hexane mixtures, to afford firstly the Z-ester (0.68g), m.p. 181°–183° C. (from ethyl acetate-hexane); $\nu$Max (KBr) 1717, 1659, 1559, and 1433 (m) cm$^{-1}$; δ (CDCl$_3$,400MHz) 0.85 (9H, s) 0.95–1.35 (5H, m), 1.82 (4H, approx.t), 2.19 (3H,s), 2.48 (1H,m), 3.87 (3H,s), 6.52 (1H, d, J10Hz), 6.92 (1H, s), and 9.73 (1H, br s). (Found: C, 63.3; H, 8.0; N, 7.7; S, 8.4; M, 364.1828. $C_{19}H_{28}N_2O_3S$ requires C, 62.6; H, 7.7; N, 7.7; S, 8.8%; M, 364.1821). Further n.m.r. analysis showed 1,4-diaxial coupling for the protons at both the 1 and 4 positions of the cyclohexane ring, allowing the 1,4-trans-configuration to be assigned. Continued elution of the column gave the E-ester (0.64g), m.p. 189°–191° C. (from ethyl acetate-hexane); $\delta$(CDCl$_3$, 400MHz), inter alia, 0.80 (9H,s), 6.84 (1H,s), and 6.90 (1H, d, J10Hz). (Found: C, 62.7; H, 8.1; N, 7.5; S, 8.4. $C_{19}H_{28}N_2O_3S$ requires C, 62.6; H, 7.7; N, 7.7; S, 8.8%).

(d)
Z-2-(2-Aminothiazol-4-yl)-3-(4-trans-t-butyl)cyclohexyl]propenoic acid

Methyl Z-[2-(2-acetamidothiazol-4-yl)-3-(trans-4-t-butyl)cyclohexyl]propenoate (364mg) was hydrolysed with 1M sodium hydroxide (5 equivalents) as described in Example 1 (e). Following acidification with 5M HCl to pH 3.7 a white solid separated; after cooling to complete precipitation, the solid was filtered, washed with a little cold water and dried to give the acid (271mg); $\nu$Max (KBr) 1617, 1562, and 1527cm$^{-1}$; $\delta$[(CD$_3$)$_2$SO, 250MHz]0.83 (9H,s) 0.90–1.25, 1.65–1.85 (9H, 2m), 2.33 (1H, m), 6.25 (1H, d, J=10Hz), 6.37 (1H, s), and 7.03 (2H, br s). (Found: M, 308.1571. $C_{16}H_{24}N_2O_2S$ requires M, 308.1559).

(e) Sodium 6$\beta$[[(Z-2-(2-aminothiazol-4-yl)-3-(4-trans t-butyl)cyclohexyl]propenamido]]penicillanate Z-[2-(2-Aminothiazol-4-yl)-3-(4-trans-t-butyl) cyclohexyl]propenoic acid (231mg) was coupled to 6-aminopenicillanic acid (194mg) using the active ester procedure as in Example 1 (f). Precipitation of crude product (305mg) at pH 3.7 as described therein and chromatography as in Example 5 (d) afforded, after pH adjustment to 6.8 and freeze-drying of appropriate fractions, the title penicillin (195mg); $\nu$Max (KBr) 1767. 1655 (sh), 1610, 1524. and 1365cm$^{-1}$; $\delta$[(CD$_3$)$_2$CO+D$_2$O, 1:1, 250MHz]0.86 (9H, s), 0.95–1.40 (5H, m), 1.59, 1.66 (6H, 2s), 1.70–2.00 (4H, m), 2.47 (1H, m), 4.24 (1H, s), 5.68 (2H. dd, J=4Hz), 6.18 (1H, d, J=10Hz), and 6.40 (1H, s); m/e 507 (MH—Na+H$^+$).

EXAMPLE 7

Sodium 6$\beta$[[Z-2-(2-aminothiazol-4-yl)-3-cyclohex-3-en-1-yl)1propenamido]]penicillanate, isomers (a)
Methyl(E,Z)2-(2-acetamidothiazol-4-yl)-3-cyclohex-3-en-1-yl)1propenoate Methyl 2-acetamidothiazol-4-acetate (4.28g), 3-cyclohexene-1-carboxaldehyde (2.42g), glacial acetic acid (1.15ml) and piperidine (1ml) were stirred in toluene (50ml) under reflux, with a water separator, for 24 hours. The reaction mixture was allowed to cool, ethyl acetate added and the mixture washed twice with water. The organic phase was dried, filtered and evaporated to an oil. This was flash chromatographed on silica gel, eluting with ethyl acetate-hexane mixtures, to give firstly the solid Z-isomer (3.1g),m.p. 163–5–165° (from ethyl acetate-hexane); $\nu$Max (nujol) 3240, 3190, 1725, 1660, and 1550cm$^{-1}$; $\delta$(CDCl$_3$, 250MHz) 1.40–2.28 (6H, m), 2.18 (3H, s), 2.85 (1H, m), 3.86 (3H, s), 5.70 (2H, m), 6.63 (1H, d, J=10Hz), 6.96 (1H, s), 10.08 (1H, br, s). (Found: C, 59.1; H, 6.0; N, 9.1. $C_{15}H_{18}N_2O_3S$ requires C, 58.8; H, 5.9; N, 9.2%). Further elution of the column gave the noncrystalline E-isomer (1.75g), which was distinguished principally by $\delta$7.00 (1H, d, J=10Hz).

(b)
Z-[2-(2-aminothiazol-4-yl)-3-(cyclohex-3-en-lyl)]-propenoic acid

Methyl Z-[2-(2-acetamidothiazol-4-yl)-3-(cyclohex-3-en-1-yl)]propenoate (1.24g) dissolved in methanol (10ml) was treated with a solution of sodium hydroxide(1g) in water (30ml). The mixture was heated under reflux for 4 hours. The reaction mixture was allowed to cool, the methanol evaporated and the cooled solution acidified with 5M HCl to pH 4. The precipitate was filtered off, washed with ice-cold water and dried to give the desired product (0.91g); $\nu$Max (KBr) 3700–2200 (br), 1690 (sh), 1630, 1560, and 1530cm$^{-1}$; $\delta$[(CD$_3$)$_2$SO, 250MHz]1.35–2.17 (6H, m), 2.68 (1H, m), 5.68 (2H, m), 6.39 (1H, d, J=10Hz), and 6.42 (1H, s). [Found: M, 250.0793. $C_{12}H_{14}N_2O_2S$ requires M, 250.0776].

(c) Sodium 6$\beta$-[[Z-2-(2-aminothiazol-4-yl)-3-(cyclohex 3-en-1-yl)1propenamido]]penicillante Z-[2-(2-Aminothiazol-4-yl)-3-(cyclohex-3-en-1-yl)]propenoic acid (0.25g) and 1-hydroxybenzotriazole mono hydrate (0.16g) were stirred in dry DMF (3ml) at 0° C. while a solution of N, N.-dicyclohexylcarbodiimide (0.22g) in DMF (2ml) was added. The mixture was allowed to regain ambient temperature. After 3 hours the mixture was filtered into a stirred solution of triethylammonium 6-aminopenicillanate (0.38g) in water (2ml) (filtered solid was washed with fresh DMF).

After stirring for 2 hours at ambient temperature the reaction mixture was maintained at −10° C. for 15 hours. The reaction mixture was evaporated to dryness and the residue partitioned between water and ether: ethyl acetate, 1:1. The aqueous phase was separated, the organic extract was backwashed with water and the whole sequence repeated once. The combined aqueous extracts were acidified to pH 3.9 when precipitation of solid (0.30g) occurred. The impure product was chromatographed on a column of silica gel. Elution with ethyl acetate: propan-2-ol: water (5:3:1) gave product-rich fractions which were concentrated to low volume, adjusted to pH7 and further chromatographed on HP 20SS. Product-rich fractons were concentrated and lyophilised to give the penicillin sodium salt (53mg) as a diastereomeric mixture, $\nu$Max (KBr) 1768, 1610, and 1530cm$^{-1}$; $\delta$[(CD$_3$) $_2$SO, 250MHz]0.8–2.15 (6H, m), 1.43 and 1.52 (6H, 2s), 2.58 (1H,m), 3.89 (1H, s), 5.36–5.48 (2H, m), 5.66 (1H, br, s), 6.13 (1H, two discrete d, J10Hz), 6.22 (1H, two discrete s), 7.05 (2H, br, s, exchanged with D$_2$O), 8.90 and 8.98 (1H, d, J=7Hz, exchanged with D$_2$O); m/e 471 (MH$^+$).

EXAMPLE 8

Cis- and trans- sodium 6$\beta$-[Z-(2-(2-aminothiazol-4-yl)-3-(4-hydroxy)cyclohexyl]propenamido]penicillanates (a) Methyl 4-(t-butyldimethylsilyl)oxy-1-cyclohexanecarboxylate Methyl 4-hydroxy-1-cyclohexanecarboxylate (7.9g; E. Hardegger, P. Plattner, and F. Blank, *Helv.Chim.*

Acta, 1944, 27, 793) dissolved in anhydrous dichloromethane (50ml) was stirred under argon at 0° C.

Following addition of t-butyldimethylsilyl chloride (8.0g) and imidazole (5.1g), the mixture was allowed to regain ambient temperature and stirring continued for 16h. The crude product was isolated by dilution with ethyl acetate, washing the organic phase with water (3x) and with brine, drying and evaporation. Silicagel chromatography afforded the silyl ether as a colourless mobile oil (12.9g), which was a 3:1 cis: trans mixture (n.m.r.); $\nu$Max (CHCl$_3$) 1730, 1465, 1440, and 1360cm$^{-1}$; $\delta$(CDCl$_3$, 250MHz), 0.00, 0.02 (6H,2s), 0.85 (9H,s), 1.05–2.35 (9H,m), 3.53, 3.86 (1H,2m), 3.63, and 3.64 (3H,2s); m/e 272 (M+).

(b) [4-(t-Butyldimethylsilyl)oxy-1-formyl]cyclohexane

Methyl 4-(t-butyldimethylsilyl)oxy-1-cyclohexanecarboxylate (1.90g) in anhydrous toluene (10ml) was stirred under argon at −95° C. and treated with a 1.5M solution of diisobutylaluminium hydride in the same solvent (4.6ml). After maintaining the same temperature for 2h, methanol (1ml) was added, followed by saturated aqueous sodium sulphate (20ml). When the mixture had regained ambient temperature, it was filtered and extracted with ether (2×25ml). The combined organic phases were washed with water and brine, dried and evaporated to give a colourless oil which was chromatographed on silica gel to afford the aldehyde (1.25g), still as a 3:1 cis: trans mixture (n.m.r.); $\nu$Max (CHCl$_3$) 1725, 1465, 1380, and 1360cm$^{-1}$; $\delta$(CDCl$_3$, 250MHz), 0.00, 0.02 (6H,2s), 0.84, 0.85 (9H,2s),.1.25–2.25 (9H,m), 3.54, 3.87 (1H,2m), 9.59, and 9.61 (1H,2d); m/e 243 (MH+).

(c) Cis- and trans- methyl Z-[2-(2-acetamidothiazol-4-yl)-3-[4-(t-butyldimethylsilyl)oxy]cyclohexyl]-propenoate

[4-(t-Butyldimethylsilyl)oxy-1-formyl]cyclohexane (0.76g) was condensed with methyl 2-acetamidothiazol-4-acetate (0.64g) as described in Example 1 (d) for 44h. The crude product (1.42g) was chromatographed on silica gel, eluting with ethyl acetate-hexane mixtures, to afford firstly the 1,4 cis-Z-isomer (71mg); $\delta$(CDCl$_3$, 250MHz) 0.04 (6H,s), 0.90 (9H,s), 1.40–1.80 (8H,m), 2.23 (3H,s), 2.61 (1H,m), 3.86 (3H,s), 3.96 (1H,m), 6.66 (1H,d,J=10Hz), 6.92 (1H,s) and 9.18 (1H,br s). Further elution gave the 1,4-trans-Z-isomer (137mg); $\nu$Max (KBr) 1725, 1700 (sh), 1661, and 1559cm$^{-1}$; $\delta$(CDCl$_3$,250MHz), inter alia, 3.55 (1H,m) and 6.47 (1H,d,J=10Hz); m/e 438 (M+), 381 (M—C$_4$H$_9$+).

(d) Methyl Z-[2-(2-acetamidothiazol-4-yl)-3-(trans-4hydroxy)cyclohexyl]propenoate Methyl Z-[2-(2-acetamidothiazol-4-yl)-3-[trans-4-(t-butyldimethylsilyl)oxy]cyclohexyl]propenoate (132mg) was heated at reflux in tetrahydrofuran (5ml) with tetra-n-butylammonium fluoride trihydrate (300mg) for 20h. The dark solution was cooled, poured into water and extracted twice with ethyl acetate, then the combined organic extracts were washed with NaHCO3 (aq), brine, dried and evaporated to give an orange gum (116mg). Chromatography on silica gel, eluting with ethyl acetate-hexane mixtures, afforded the hydroxy ester (69mg) (Found: M, 324.1145. C$_{15}$H$_{20}$N$_2$O$_4$S requires M, 324.1144); $\delta$[(CD$_3$)$_2$CO, 250MHz]1.15$\propto$1.40, 1.70–2.05 (8H,2m), 2.26 (3H,s), 2.47 (1H,m), 3.50 (1H,m), 3.84 (3H,s), 6.55 (1H,d,J=10Hz), 6.98 (1H,s), and 11.00 (1H,br s).

(e) Z-[2-(2-Aminothiazol-4-yl)-3-(trans-4-hydroxyl)-cyclohexyl]propenoic acid.

Methyl Z-[2-(2-acetamidothiazol-4-yl)-3-(trans-4-hydroxy)cyclohexyl]propenoate (65mg) was hydrolysed with 1M sodium hydroxide (5 equivalents) as described in Example 1(e). After acidification to pH2, the aqueous solution was saturated with sodium chloride and extracted with tetrahydrofuran (5×). The combined extracts were rigorously dried and evaporated to a semi-solid which was chromatographed on silica gel, eluting with ethyl acetate: isopropanol:water mixtures, to afford the acid as a colourless powder (54mg); $\nu$max (KBr) 1628, 1569, 1530(sh), 1449, and 1415cm$^{-1}$; $\delta$[(CD$_3$)SO,250MHz]1.12–1.82 (8H,3m), 2.37 (1H,m), 3.36 (1H,m,visible on D$_2$O exch.), 4.54 (1H,br s,D$_2$O exch.), 6.13 (1H,d,J10Hz), 6.39 (1H,s), and 6.98 (2H,br s,D$_2$O exch.); m/e 269 (MH+).

(f) Sodium 6[Z-2-(2-aminothiazol-4-yl)-3-(trans-4hydroxy)cyclohexyl]propenamido]penicillanate Z-[2-(2-Aminothiazol-4-yl)-3-(trans-4-hydroxy)cyclohexyl]propenoic acid (45mg) was coupled to 6aminopenicillanic acid (40mg) using the active ester procedure as described in Example 1 (f). After acidification with 2M HCl to pH2 the aqueous phase was saturated with sodium chloride, then extracted with ethyl acetate: tetrahydrofuran, 1:1 (2×) and tetrahydrofuran (2×). The organic extract was dried as far as possible over magnesium sulphate and filtered, then water was added and the pH of the aqueous phase adjusted to 7.0 with aqueous NaHCO$_3$. Separation and lyophilisation of the aqueous phase followed by chromatography of the crude product on HP20SS, eluting with water:acetone mixtures, then pooling and evaporating appropriate fractions, afforded the penicillin (50mg); $\nu$Max (KBr) 1763, 1660(sh), 1609, 1522, and 1450(w)cm$^{-1}$; $\delta$(D$_2$O,250MHz) 1.10–2.00 (8H,m), 1.50, 1.59 (6H,2s), 2.24 (1H,m), 3.58 (1H,br s), 4.22 (1H,s), 5.59 (2H,dd), 6.08 (1H,d,J10.5Hz), and 6.44 (1H,s); m/e 489 (MH+) and 511 (MNa+).

(g) Z-[2-(2-Aminothiazol-4-yl)-3-(cis-4-hydroxy)cyclohexyl]propenoic acid

Methyl Z-[2-(2-acetamidothiazol-4-yl)-3-[cis-4-(t-butyldimethylsilyl)oxy]cyclohexyl]propenoate (71mg) was desilylated using tetra-n-butylammonium fluoride trihydrate (252mg) as described in Example 8(d). After chromatography the product was at once hydrolysed using 1M sodium hydroxide (5 equivalents) as described in Example 1(e). After acidification to pH2 with 2M HCl the aqueous phase was saturated with sodium chloride and extracted with tetrahydrofuran (4x). The combined organic extracts were dried and evaporated to give crude product which was chromatographed on silica gel, eluting with ethyl acetate:isopropanol:water mixtures, to give the acid (29mg); $\delta$[(CD$_3$)$_2$SO,250MHz]1.30–1.70 (8H,m), 2.50 (1H,m,partly solvent-obscured), 3.73 (1H,m), 6.32 (1H,d,J=10Hz), 6.38 (1H,s), and 7.01 (2H,s); m/e 224 (M—CO$_2$+).

(h) Sodium 6β-[Z-2-(2-aminothiazol-4-yl)-3-(cis-4hydroxy)cyclohexyl]propenamido]penicillanate Z-[2-(2-Aminothiazol-4-yl)-3-(cis-4-hydroxy)cyclohexyl]propenoic acid (27mg) was coupled to 6-aminopenicillanic acid (24mg) using the active ester procedure as described in Example 1(f). Workup and chromatography as described in Example 9(f) gave the title penicillin (19mg); νMax (KBr) 1765, 1655(sh), 1610, and 1525cm$^{-1}$; δ(D$_2$O, 250MHz) 1.40–1.80 (8H,m), 1.49, 1.59 (6H,2s), 2 37 (1H,m), 3.96 (1H,m), 4.21 (1H,s), 5.59 (2H,dd), 6.24 (1H,d,J=10.5Hz), and 6.46 (1H,s); m/e 467 (M—Na+H+) and 489 (MH+).

EXAMPLE 9

Sodium 6β-[Z-[2-(2-aminothiazol-4-yl)-3-(4dichloromethylene)-cyclohexyl]propenamido]penicillanate

(a) Methyl 4-oxo-1-cyclohexanecarboxylate

A 1M solution of chromium trioxide in dilute aqueous sulphuric acid (17ml) was added dropwise at 20° C. to a stirred solution of methyl 4-hydroxy-1-cyclohexanecarboxylate (4.0g) in acetone (30ml). Excess oxidant was destroyed by adding propan-2-ol dropwise until a green coloration persisted. The solution was then diluted with water and extracted with ether (2x), the combined organic extracts were washed with water and brine, then dried and evaporated. Kugelrohr distillation of the residue afforded the ketoester (3.08g) (W.H. Perkin, jr., J.Chem.Soc., 1904, 416); δ(CDCl$_3$, 90MHz) 1.50–2.60 (8H,m), 2.78 (1H,m), and 3.70 (3H,s).

(b) (4-Dichloromethylene-1-formyl)cyclohexane

Methyl 4-oxo-1-cyclohexanecarboxylate (1.04g) was stirred with triphenylphosphine (6.98g) in anhydrous acetonitrile (10ml) under argon at 0° C. Carbon tetrachloride (1.29ml,2.05g) was added and the mixture, which gradually became a yellow solution, was allowed to warm to ambient temperature. After 3h, when no triphenylphosphine was detected by t.l.c., the solution was poured into water and extracted twice with ether, then the combined organic extracts were washed twice with water and with brine, dried and evaporated to give crude product. Chromatography gave a colourless oil(1.28g); δ(CDCl$_3$), 60MHz) 1.50–3.20 (9H,m) and 3.75 (3H,s). This material was dissolved in anhydrous toluene (10ml) and reduced with 1.5M diisobutylaluminium hydride (3.8ml) as described in Example 8(b). Chromatography afforded the aldehyde (0.96g); νMax (CHCl$_3$) 1725, 1685 (m—w), and 1450(w)cm$^{-1}$; δ(CDCl$_3$,90Hz), 1.35–2.90 (9H,m) and 9.63 (1H,br s). (Found: M, 192.0106. C$_8$H$_{10}$Cl$_2$O requires M, 192.0109).

(c) Methyl (E,Z)-2-(2-acetamidothiazol-4-yl)-3-(4dichloromethylene)cyclohexyl]propenoate (4-Dichloromethylene-1-formyl)cyclohexane (0.85g) was condensed with methyl 2-acetamidothiazol-4-acetate (0.94g) as described in Example 1(d) but using benzene (10ml) at reflux for 48h. Chromatography of crude product (2.05g) on silica, eluting with ethyl acetate-hexane mixtures, afforded firstly the Z-ester (409mg), m.p.>230° C. (from ethyl acetate-hexane); νmax (KBr) 1739, 1695(W), 1646, and 1552cm$^{-1}$; δ[(CD$_3$)CO, 250MHz]1.31, 1.85–2.20 (8H,2m), 2.27 (3H,s), 2.77 (1H,m), 3.85 (3H,s), 6.56 (1H,d,J10Hz), and 7.01 (1H,s).

(Found: C, 49.7; H, 4.5; N, 7.1; Cl, 17.9; S, 8.2. C$_{16}$H$_{18}$C$_{12}$N$_2$O$_3$S requires C, 49.4; H,4.6; N, 7.2; Cl, 18.3; S, 8.2%). Further elution afforded the E-ester (567mg), δ(CDCl$_3$,90MHz), inter alia, 6.84 (1H,d,J=10Hz) and 6.91 (1H,s).

(d) Z-[2-(2-Aminothiazol-4-yl)-3-(4-dichloromethylene)cyclohexyl]propenoic acid Methyl Z-[2-(2-acetamidothiazol-4-yl)-3-(4dichloromethylene)cyclohexyl]propenoate (190mg) was hydrolysed using 1M sodium hydroxide (5 equivalents) as described in Example 1(e). After acidification to pH4 with 5M HCl the precipitate was filtered, washed with water and dried to give the acid (119mg); νMax (KBr) 1690(sh), 1616, 1562, and 1527cm$^{-1}$; δ[(CD$_3$)$_2$SO,250MHz], 1.15–2.90 (8H,3m), 2.62 (1H,m), 6.23 (1H,d,J=10Hz), 6.41 (1H,s), and 7.06 (2H,br s, D$_2$O exch.). (Found: M, 322.0153. C$_{13}$H$_{14}$Cl$_2$N$_2$O$_2$S requires M. 322.0153).

(e) Sodium 6β-[Z-[2-(2-aminothiaZOl-4-yl)-3-(4dichloromethylene)cyclohexyl]propenamido]penicillanate Z-[2-(2-Aminothiazol-4-yl)-3-(4-dichloromethylene)-cyclohexyl]propenoic acid (105mg) was coupled to 6-aminopenicillanic acid (75mg) using the active ester procedure [Example (1f)]After acidification to pH 3.5 with 2M HCl the fine yellow precipitate was filtered, washed with water and dried to afford crude product (133mg). Chromatography on silica gel, eluting with ethyl acetate:isopropanol:water mixtures, followed by pooling of appropriate fractions, concentration to low volume, adjusting to pH7.0 using aqueous NaHCO3 and freeze-drying, yielded the penicillin (88mg); νmax 1767, 1660(sh), 1609, and 1528cm$^{-1}$; δ[(CD$_3$)$_2$SO+D$_2$O,1:1, 250MHz], 1.15–2.95 (8H,3m), 1.49, 1.58 (6H,2s), 2.50(1H,m), 4.10 (1H,s), 5.54 (2H,dd,J=4Hz), 6.08 (1H,d,J=10Hz), and 6.38 (1H,s); m/e 530 and 532 (M—Na+H+).

EXAMPLE 10

Sodium 6β[Z-2-(2-aminothiazol-4-yl)-3-(trans-4phenyl)cyclohexyl]propenamido]penicillanate

(a) Cis- and trans-4-phenylcyclohexane carboxaldehyde (Methoxymethyl)triphenylphosphonium chloride (5.14g) was suspended in anhydrous tetrahydrofuran (THF) (15ml) and stirred under argon at 0° C. A solution of potassium t-butoxide (1.68g) in THF (15ml) was added dropwise and stirring continued at the same temperature for 0.5h. To the resulting dark red near- solution was added a solution of 4-phenylcyclohexanone (2.61g) in THF (4ml), then the mixture was allowed to regain ambient temperature and stirring continued for 16h. Workup and chromatography as described in Example 5(a) gave 4-phenyl-1-(methoxymethylene)cyclohexane (1.59g) contaminated with a little triphenylphosphine; δ(CDCl$_3$,60MHz), inter alia, 3.55 (3H,s), 5.90 (1H,br s), and 7.35 (6H,m). This material in THF (8ml) and water (2ml) was stirred at 20° C. with toluene sulphonic acid hydrate (2.50g) for 8h. Workup as described in Example 5(b) followed by chromatography on silica gel, eluting with ethyl acetate in hexane mixtures, gave the aldehyde (1.29g) as an approximately 2:3 cis:trans mixture; νMax (CHCl$_3$) 1725, 1605, 1495, and 1450cm⁻¹; δ(CDCl₃,250MHz), 1.3–2.60 (10H,m), 7.15–7.35 (5H,m), 9.68, and 9.79 (1H,d,J=1.5Hz and s). [M. Carissimi et al., Farmaco (Pavia) Ed.Sci., 1965, 20. 106 (Chem.Abs., 1965, 62, 14560)].

(b) Methyl (E,Z)-[2-(2-acetamidothiazol-4-yl)-3-(trans-4-phenyl)-cyclohexyl]propenoate Cis-/trans-4-phenylcyclohexane carboxaldehyde (0.56g) was condensed with methyl 2-acetamidothiazol-4-acetate (0.64g) as described in Example 1(d). Chromatography of the crude product (1.07g) on silica, eluting with ethyl acetate-hexane mixtures, afforded firstly the Z-ester (270mg), m.p. 145°–147° C.; δ(CDCl₃,250MHz) 1.20–1.60, 1.85–2.00 (8H,2m), 2.22 (3H,s), 2.51 (1H,m), 2.68 (1H,m), 3.89 (3H,s), 6.60 (1H,d,J10Hz), 6.95 (1H,s), 7.15–7.35 (5H,m), and 9.54 (1H,br s). (Found:M, 384.1511. $C_{21}H_{24}N_2O_3S$ requires M, 384.1508). Further elution gave the E-ester (234mg), δ(CDCl₃,90MHz), inter alia, 6.85 (1H,s) and 6.93 (1H,d,J10Hz).

(c) Z-[2-(2-Aminothiazol-4-yl)-3-(trans-4-phenyl)-cyclohexyl]propenoic acid

Methyl Z-[2-(2-acetamidothiazol-4-yl)-3-(trans-4-phenyl)cyclohexyl]propenoate (155mg) was hydrolysed using 1M NaOH (5 equivalents) as described in Example 1(e). After acidification with 5M HCl to pH 3.5 the precipitate was filtered, washed with water and dried to afford the acid (97mg); νmax (KBr) 1695(sh), 1616, 1560, 1528, and 149cm⁻¹; δ[(CD₃)₂SO,250MHz]1.20–1.90 (8H,m), 2.40–2.60 (2H,2m,partly solvent-obscured), 6.32 (1H,d,J=10Hz), 6.40 (1H,s), 7.05 (2H,br s,D₂O exch.), and 7.10–7.35 (5H,m). (Found:M,328.1257. $C_{18}H_{20}N_2O_2S$ requires M,328.1245).

(d) Sodium 6β-Z-[2-(2-aminothiazol-4-yl)-3-(trans-4phenyl)cyclohexyl]propenamido]penicillanate Z-[2-(2-Aminothiazol-4-yl)-3-(trans-4-phenyl)cyclohexyl]propenoic acid (82mg) was coupled to 6aminopencillanic acid (60mg) using the active ester procedure [Example 1(f)]. After acidification to pH 3.5 the precipitate was filtered, washed with water and dried to give the crude product as a yellow powder (107mg). Chromatography followed by conversion to sodium salt as described in Example 10(e) afforded the title penicillin (89mg); νMax (KBr) 1767, 1660(sh), 1609, and 1526cm⁻¹; δ[(CD₃)₂SO,250MHz]1.20–1.80 (8H,2m), 1.46, 1.52 (6H,2s), 2.46 (2H,m, partly solvent-obscured), 3.85 (1H,s), 5.47 (2H,m,dd,J=3.6Hz on D₂O exch.), 6.09 (1H,d,J=10Hz), 6.24 (1H,s), 7.03 (2H,br s,D₂O exch.), 7.15–7.35 (5H,m), and 8.90 (1H,br d,D₂O exch.); m/e 527 (M—Na+H+).

EXAMPLE 11

Sodium 6β-Z-2-(2-chloroacetylaminothiazol-4-yl)-3-(cyclohex-1-enyl]propenamido]penicillanate

(a) Methyl (E,Z)-(2-(2-chloro-1-oxoethyl)-3-(cyclohex-1-enyl)]-propenoate

Methyl 4-chloroacetoacetate (10.60g), cyclohex-1-ene-1-carboxaldehyde (I. Heilbron, E.R.H. Jones, R.W. Richardson, and F. Sondheimer, J.Chem.Soc., 1949, 737) (7.33g), piperidine (2ml) and glacial acetic acid (2ml), were stirred in benzene (70ml) under reflux and under argon, with a water separator, for 1½h. The reaction at this time appeared complete by t.l.c. The reaction mixture was allowed to cool and taken up in ethyl acetate. This solution was washed twice with water, dried, filtered and evaporated to an oil which was flash chromatographed on silica eluting with ethyl acetate-hexane mixtues to give the desired product (10.78g) as a pale yellow oil (3:1 isomer ratio); δ(CDCl₃,250MHz), inter alia, 3.76 and 3.86 (3H,2s).

(b) Methyl Z-[2-(2-aminothiazol-4-yl)-3-(cyclohex-1-enyl)]-propenoate, hydrochloride Methyl (E,Z)-2-(2-chloro-1-oxoethyl)-3-(cyclohex1-enyl)]propenoate (2.20g) and thiourea (0.69g) were stirred in methanol (20ml) under relux for 1.75h; the reaction then appeared complete by t.l.c. The solution was concentrated and treated with ether to give the crystalline Z-isomer (1.89g), m.p. 179°–180.5° C. (from methanol-chloroform-hexane); νMax (nujol) 1700 and 1610cm⁻¹; δ[(CD₃)₂SO,250MHz]1.50 (4H,m), 1.79 (2H,m), 2.23 (2H,m), 3.70 (3H,s), 6.52 (1H,br s), 6.76 (1H,s), 7.47 (1H,s), and 9.35 (2H,br s, D₂O exch.). (Found: C, 52.0; H, 5.7; N, 9.3; S, 10.4 $C_{13}H_{17}ClN_2O_2S$ requires C, 51.9; H,5.7; N, 9.3; S, 10.7%).

(c) Z-2-(2-Aminothiazol-4-yl)-3-(cyclohex-1-enyl)]-propenoic acid

Methyl Z-[2-(2-aminothiazol-4-yl)-3-(cyclohex-1enyl)]propenoate, hydrochloride (1.51g) and sodium hydroxide (0.93g) were stirred in aqueous methanol (1:1, 20ml) under reflux for 1.5h. The mixture was cooled, concentrated, diluted with water and the aqueous solution was acidified with 5M HCl to pH4, when a fine precipitate formed. The precipitate was filtered off, washed with ice-cold water, then with ether, and dried to give the desired product (0.85g), m.p. 146°–149° C.; νMax (KBr) 3600–2100 (br), 1620, 1570, and 1535cm⁻¹; δ[(CD₃)₂SO,250MHz], 1.43 (4H,m), 1.76 (2H,m), 2.14 (2H,m), 6.20 (1H,br s), 6.28 (1H,s), 6.88 (2H,broads,D₂O exch.), and 7.20 (1H,s). [Found: M, 250.0779. $C_{12}H_{14}N_2O_2S$ requires M, 250.0776].

(d) Z-[2-(2-Chloroacetylaminothiazol-4-yl)-3-(cyclohex-1-enyl)]propenoic acid Z-[2-(2-Aminothiazol-4-yl)-3-(cyclohex-1-enyl)]-propenoic acid (0.80g) and type 4A molecular sieves (1.5g) were stirred in N,N-dimethylacetamide (9ml) at ambient temperature whilst chloroacetyl chloride (1.5ml) was added. After 1h t.l.c. indicated the reaction was complete. The mixture was filtered and the molecular sieves washed with ethyl acetate. The filtrate was evaporated to dryness and the resulting brown oil stirred with saturated aqueous NaHCO₃. The mixture was layered with ethyl acetate and acidified with 5M HCl. The organic phase was washed with water, dried and evaporated to a solid which on trituration with ether gave the desired product (0.73g), m.p. 182°–183° C.; νMax (nujol) 3600–2100, 1710, 1685, 1650, 1605, and 1560cm⁻¹; δ[(CD₃)₂SO,250MHz] 1.40 (4H,m), 1.55 (2H,m), 2.14 (2H,m), 4.38 (2H,s), 6.26 (1H,br s), 7.03 (1H,s), and 7.34 (1H,s). [Found: M, 326.0491. $C_{14}H_{15}ClN_2O_3S$ requires M, 326.0491]. (Found: C, 51.5; H, 4.6; N, 8.5; S, 9.6. $C_{14}H_{15}ClN_2O_3S$ requires C, 51.5; H, 4.6; N, 8.6; S, 9.8%).

27

(e) Sodium 6β-[Z-2-(2-chloroacetylaminothiazol-4-yl)-3-(cyclohex-1-enyl)]propenamido]penicillanate Z-[2-(2-Chloroacetylaminothiazol-4-yl)-3-(cyclohex-1-enyl)]propenoic acid (0.327g) and triethylamine (0.16ml) were stirred in dry dichloromethane (6ml) at −25° C. while a solution of thionyl chloride (0.125g) in dichloromethane was slowly added. The mixture was allowed to warm to ambient temperature. After 1.5h. the solution was evaporated to dryness, then redissolved in dry dichloromethane (10ml) and slowly added to a stirred solution of 6-aminopenicillanic acid triethylammonium salt (0.32g) and triethylamine (0.15ml in dichloromethane (10ml) at 0° C. mixture was allowed to warm to ambient temperature. After 3h, t.l.c. indicated complete reaction. The solution was evaporated and flash chromatographed on silica eluting with ethyl acetate: propan-2-ol:water mixtures. Penicillin-containing fractions were evaporated to dryness and the product redissolved in aqueous tetrahydrofuran. The pH of the penicillin solution was adjusted to 7 by addition of aqueous $NaHCO_3$. Concentration to low volume, then lyophilisation, gave the title penicillin (0.456g); $\nu$Max (KBr), inter alia, 1763cm$^{-1}$; δ(CD$_3$)$_2$SO,250MHz]1.-25-1.70 (6H,m), 1.30, 1.40 (6H,2s), 2.16 (2H,br s), 3.94 (1H,s), 4.34 (2H,s), 5.40-5.70 (2H,m), 6.26 (1H,broads), 7.11 (1H,s), and 7.26 (1H,s).

EXAMPLE 12

Sodium 6β-[Z-[2-(2-aminothiazol-4-yl)-3-(cyclohex-1-enyl)]-propenamido]penicillanate Sodium 6'-[Z-[2-(2-chloroacetylaminothiazol-4-yl)3-(cyclohex-1-enyl)]propenamido]penicillanate (0.385g) and sodium N-methyldithiocarbamate (0.116g) were stirred in water (15ml) at ambient temperature. After 4h the mixture was evaporated, redissolved in a 1:1 propan-2-ol:water mixture and the solution flash chromatographed on silica, eluting with ethyl acetate:propan-2-ol:water mixtures. The product containing fractions were evaporated to dryness, the penicillin redissolved in water and the pH adjusted to 7.5 by addition of aqueous NaHC03. Lyophilisation gave the title penicillin (0.187g); $\nu$Max (KBr) 1762, 1658(sh), 1608, and 1509cm$^-$; δ[(CD$_3$)$_2$SO,250MHz]1.30–1.60 (4H,m), 1.41, 1.45 (6H,2s), 1.78 (2H,br s) 2.16 (2H, br s), 3.96 (1H,S), 5.42–5.52 (2H,m), 6.20 (1H,broad s), 6.42 (1H,s), 7.12 (1H,br s,D$_2$O exch.), 7.16 (1H,s), and 7.46 (1H,m,D$_2$O exch.).

Using the procedures set out above, the following compounds were also made:

Sodium 6β-[Z-[2-(2-aminothiazol-4-yl)-3-(trans-4trifluoromethyl)cyclohexyl]propenamido]penicillante.

Sodium 6β-[Z-[2-(2-aminothiazol-4-yl)-3-(4-chlorocyclohex-3- en-1-yl)]propenamido]penicillanate (1:1 epimeric mixture].

Sodium 6β-[Z-[2-(2-aminothiazol-4-yl)-3-(trans-4-methoxy)cyclohexyl]propenamido]penicillanate.

| | In vitro Biological Data | |
|---|---|---|
| organism | Example No. 1 | Example No. 6 |
| E.coli 10418 | 0.12 | 0.25 |
| E.coli JT425 | 16.00 | 16.00 |
| E.coli ESS | <0.03 | <0.03 |
| E.coli 1077 | 8.00 | 8.00 |

-continued

| | In vitro Biological Data | |
|---|---|---|
| organism | Example No. 1 | Example No. 6 |
| K.pneumoniae T767 | 16.00 | 8.00 |
| P.mirabilis C977 | 8.00 | 4.00 |
| M.morganii T361 | 8.00 | 4.00 |
| H.influenzae Q1 | <0.03 | 0.12 |
| H.influenzae NEMC | 0.25 | 1.00 |
| B.catarrhalis RAVASIO | 0.50 | 0.50 |
| PS.aeruginosa 10662 | 16.00 | 32.00 |
| S.aureus OXFORD | 0.50 | 0.50 |
| S.aureus RUSSELL | 2.00 | 1.00 |
| S.aureus MB9 | 2.00 | 2.00 |
| S.aureus V573 | 4.00 | 4.00 |
| S.epidermidis PHLN20 | 0.50 | 2.00 |
| Str.pyogenes CN10 | <0.03 | 0.06 |
| Str.agalactiae 2798 | 0.25 | 1.00 |
| Str.pneumoniae PU7 | 2.00 | 4.00 |
| Str.pneumoniae 1761 | <0.03 | <0.03 |
| Str.faecalis I | 32.00 | 32.00 |

What is claimed is:

1. A compound of formula (I) or a pharmaceutically acceptable salt or in-vivo hydrolysable ester thereof:

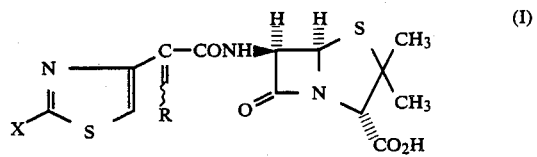

wherein X is hydrogen or a group NHR$^1$, wherein R$^1$ is hydrogen or an amino protecting group, and R is optionally substituted cycloalkyl of 5 to 8 carbon atoms or cycloalkenyl of 5 to 8 carbon atoms.

2. A compound according to claim 1, wherein R is cycloalkyl of 5 to 8 carbon atoms.

3. A compound according to claim 1, wherein R is selected from the group consisting of:
cyclohexyl;
cyclooctyl;
2-methylcyclohexyl;
4-trans-t-butylcyclohexyl;
cyclohex-3-en-1-yl;
4-hydroxycyclohexyl;
4-dichloromethylenecyclohexyl;
trans-4-phenylcyclohexyl; and
cyclohex-1-enyl.

4. A compound according to claim 1 which is the syn-isomer of formula (IA), or a pharmaceutically acceptable salt or in-vivo hydrolysable ester thereof:

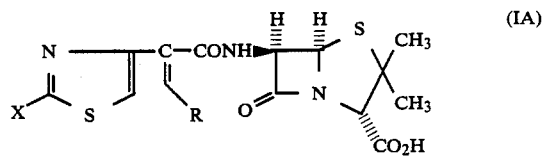

wherein X is hydrogen or a group NHR$^1$, wherein R$^1$ is hydrogen or an amino protecting group, and R is optionally substituted cycloalkyl of 5 to 8 carbon atoms or cycloalkenyl of 5 to 8 carbon atoms.

5. A compound according to claim 1 in the form of the α-acetoxyethyl ester thereof.

6. A compound selected from the group consisting of:
6β-[Z-2-(2-aminothiazol-4-yl)-3-cyclohexyl]-propenamidopenicillanic acid;

6β-[Z-2-(2-aminothiazol-4-yl)-3-cyclooctyl]-
propenamidopenicillanic acid;
6β-[Z-[2-(thiazol-4-yl)-3-cyclohexyl]-
propenamidopenicillanic acid;
1-acetoxyethyl  6β-Z-[2-(2-aminothiazol-4-yl)-3-cyclohexyl]propenamidopenicillanate;
6β[[Z-2-(2aminothiazol-4-yl)-3-(2-methyl) cyclohexyl]-propenamido]penicillanic acid;
6β-[[Z-2-(2-aminothiazol-4-yl)-3-(4-trans-t-butyl)cyclohexyl]propenamido]penicillanic acid;
6β-[[Z-2-(2-aminothiazol-4-yl)-3-cyclohex-3-en-1-yl)propenamido]penicillanic acid;
cis- and trans- 6β-[Z-[2-(2-aminothiazol-4-yl)-3-(4-hydroxyl)cyclohexyl]propenamido]penicillanic acid;
6β-[Z-[2-(2-aminothiazol-4-yl)-3-(4-dichloromethylene)cyclohexyl]propenamido]penicillanic acid;
6β[Z-[2-(2-aminothiazol-4-yl)-3-(trans-4-phenyl)cyclohexyl]propenamido]penicillanic acid;
6β-[Z-[2-(2-chloroacetylaminothiazol-4-yl)-3-(cyclohex-1-enyl)]propenamido]penicillanic acid; and
6β-[Z-[2-(2-aminothiazol-4-yl)-3-(cyclohex-1-enyl)]-propenamido]penicillanic acid;
or a pharmaceutically acceptable salt or in vivo hydrolysable ester thereof.

7. A process for the preparation of a compound according to claim 1, which process comprises treating a compound of formula (II) or salt thereof;

(II)

wherein the amino group is optionally substituted with a group which permits acylation to take place, and R³ is hydrogen or a readily removable carboxyl blocking group; with an acylating agent derived from the acid of formula (III):

$$Y-\underset{\underset{R}{\|}}{C}-CO_2H \quad (III)$$

wherein Y is a group of formula:
or a group which is convertable thereto, and X is hydrogen or a group NHR¹, wherein R¹ is hydrogen or an amino protecting group, and R is optionally substituted cycloalkyl of 5 to 8 carbon atoms or cycloalkenyl of 5 to 8 carbon atoms.

8. A pharmaceutical composition useful for treating bacterial infections in human and non-human animals which comprises an anti-bacterially effective amount of a compound f formula (I):

(I)

or a pharmaceutically acceptable salt or in-vivo hydrolysable ester thereof wherein X is hydrogen or a group NHR¹, wherein R¹ is hydrogen or an amino protecting group, and R is optionally substituted cycloalkyl of 5 to 8 carbon atoms or cycloalkenyl, in combination with a pharmaceutically acceptable carrier.

9. A composition according to claim 8 wherein R is cycloalkyl of 5 to 8 carbon atoms.

10. A composition according to claim 8, wherein R is selected from the group consisting of:
cyclohexyl;
cyclooctyl;
2-methylcyclohexyl;
4-trans-t-butylcyclohexyl;
cyclohex-3-en-1-yl;
4-hydroxycyclohexyl;
4-dichloromethylenecyclohexyl;
trans-4-phenylcyclohexyl; and
cyclohex-1-enyl.

11. A composition according to claim 8 wherein the compound is the syn-isomer of formula (IA);

(IA)

or a pharmaceutically acceptable salt or in-vivo hydrolysable ester thereof wherein X is hydrogen or a group NHR¹, wherein R¹ is hydrogen or an amino protecting group, and R is optionally substituted cycloalkyl of 5 to 8 carbon atoms or cycloalkenyl.

12. A composition according to claim 8 wherein the compound is in the form of the β-acetoxyethyl ester thereof.

13. A composition according to claim 8 wherein the compound is selected from the group consisting of:
6β-[Z-2-(2-aminothiazol-4-yl)-3-cyclohexyl]-
propenamidopenicillanic acid;
6β-[Z-(2-aminothiazol-4-yl)-3-cyclooctyl]-
propenamidopenicillanic acid;
6-β-Z-[2-(thiazol-4-yl)-3-cyclohexyl]-
propenamidopenicillanic acid;
1-acetoxyethyl  6β-Z-[2-(2-aminothiazol-4-yl)-3-cyclohexyl]propenamidopenicillanate;
6-β[[Z-2-(2-aminothiazol-4-yl)-3-(2methyl) cyclohexyl]-propenamido]penicillanic acid;
6β-[[Z-2-(2-aminothiazol-4-yl)-3-(4-trans-t-butyl)cyclohexyl]propenamido]penicillanic acid; 6β-[[Z-2-(2-aminothiazol-4-yl))-3-cyclohex-3-en-1-yl)]propenamido]penicillanic acid;
cis- and trans- 6β-[Z-[2-(2-aminothiazol-4-yl)-3-94-hydroxyl)cyclohexyl]propenamido]penicillanic acid;
6β-[Z-[2-(2-aminothiazol-4-yl)-3-(4-dichloromethylene)cyclohexyl]propenamido]penicillanic acid;
6β[Z-[2-(2-aminothiazol-4-yl)-3-(trans-4-phenyl)cyclohexyl]propenamido]penicillanic acid;
6β-[Z-[2-(2-chloracetylaminothiazol-4-yl)-3-(cyclohex-1-enyl)]propenamido]penicillanic acid; and
6β-[Z-[2-(2-aminothiazol-4-yl)-3-(cyclohex-1-enyl)]-propenamido]penicillanic acid; or a pharmaceutically acceptable salt or in vivo hydrolysable ester thereof.

14. A method for the treatment of bacterial infections in human and non-human animals, which comprises administering to a human or non-human animal in need thereof an anti-bacterially effective amount of a compound of formula (I):

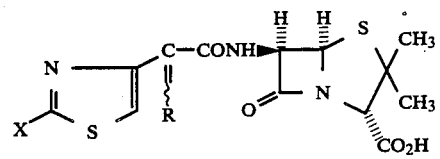

or a pharmaceutically acceptable salt or in-vivo hydrolysable ester thereof, wherein X is hydrogen or a group NHR¹, wherein R¹ is hydrogen or an amino protecting group, and R is optionally cycloalkyl of 5 to 8 carbon atoms or cycloalkenyl of 5 to 8 carbon atoms.

15. A method according to claim 14, wherein R is cycloalkyl of 5 to 8 carbon atoms.

16. A method according to claim 14, wherein R is selected from the group consisting of:

cyclohexyl;

cyclooctyl;

2-methylcyclohexyl;

4-trans-t-butylcyclohexyl;

cyclohex-3-en-1-yl;

4-hydroxycyclohexyl;

4-dichloromethylenecyclohexyl;

trans-4-phenylcyclohexyl; and cyclohex-1-enyl.

17. A method according to claim 16 which is the syn-isomer of formula (IA):

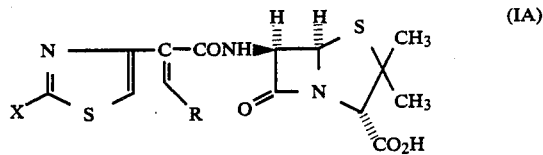

or a pharmaceutically acceptable salt or in-vivo hydrolysable ester thereof wherein X is hydrogen or a group NHR¹, wherein R¹ is hydrogen or an amino protecting group, and R is optionally cycloalkyl of 5 to 8 carbon atoms or cycloalkenyl of 5 to 8 carbon atoms.

18. A method according to claim 14 wherein the compound is in the form of the β-acetoxyethyl ester thereof.

19. A method according to claim 14, wherein the compound is selected from the group consisting of:

6β[Z-2-(2-aminothiazol-4-yl)-3-cyclohexyl]-propenamidopenicillanic acid;

6β-[Z-(2-aminothiazol-4-yl)-3-cyclooctyl]-propenamidopenicillanic acid;

6β-[2-(thiazol-4-yl)-3-cyclohexyl]-propenamidopenicillanic acid;

1-acetoxyethyl 6β-Z-[2-(amionthiazol-4-yl)-3-cyclohexyl]propenamidopenicillanate;

6β-[[Z-2-(2-aminothiazol-4-yl)-3-(2-methyl) cyclohexyl]-propenamido]penicillanic acid;

6β-[[Z-2-(2-aminothiazol-4-yl)-3-)4-trans-t-butyl)cyclohexyl-9 propenamido]penicillanic acid;

6-β-[[Z-2-(2-aminothiazol-4-yl)-3-cyclohex-3-en-1-yl)]propenamido]penicillanic acid;

cis- and trans- 6β-[Z-[2-(2-aminothiazol-4-yl)-3-(4-hydroxy)cyclohexyl]propenamido]penicillanic acid;

6β-[Z-[2-(2-aminothiazol-4-yl)-3-(4-dichloromethylene)cyclohexyl]propenamido]penicillanic acid;

6β-[Z-2-(2-aminothiazol-4-yl)-3-(trans-4-phenyl)cyclohexyl]propenamido]penicillanic acid;

6β-[Z-[2-chloracetylamionthiazol-4-yl)-3-(cyclohex-1-enyl)]propenamido]penicillanic acid; and 6β-[Z-[2-(2-aminothiazol-4-yl)-3-(cyclohex-1-enyl)]propenamido]penicillanic acid;

or a pharmaceutically acceptable salt or in vivo hydrolysable ester thereof.

* * * * *